US011166685B2

(12) United States Patent
Takayasu et al.

(10) Patent No.: US 11,166,685 B2
(45) Date of Patent: Nov. 9, 2021

(54) RADIATION DETECTOR AND RADIATION DETECTOR MODULE

(71) Applicant: CANON MEDICAL SYSTEMS CORPORATION, Otawara (JP)

(72) Inventors: Masao Takayasu, Shimotsuke (JP); Minoru Horinouchi, Otawara (JP); Akira Nishijima, Nasushiobara (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 3 days.

(21) Appl. No.: 16/525,851

(22) Filed: Jul. 30, 2019

(65) Prior Publication Data

US 2020/0037968 A1    Feb. 6, 2020

(30) Foreign Application Priority Data

Aug. 3, 2018    (JP) .............................. JP2018-146698

(51) Int. Cl.
*A61B 6/03*     (2006.01)
*A61B 6/00*     (2006.01)
*G01T 7/00*     (2006.01)
*G01T 1/20*     (2006.01)

(52) U.S. Cl.
CPC ............ *A61B 6/4266* (2013.01); *A61B 6/032* (2013.01); *A61B 6/035* (2013.01); *A61B 6/4035* (2013.01); *A61B 6/42* (2013.01); *A61B 6/4208* (2013.01); *A61B 6/4291* (2013.01); *A61B 6/44* (2013.01); *A61B 6/4411* (2013.01); *A61B 6/4429* (2013.01); *A61B 6/4435* (2013.01); *A61B 6/4447* (2013.01); *A61B 6/5205* (2013.01); *G01T 1/2018* (2013.01); *G01T 7/00* (2013.01)

(58) Field of Classification Search
CPC ........... A61B 6/032; A61B 6/035; A61B 6/42; A61B 6/4208; A61B 6/4233; A61B 6/4266; A61B 6/44; A61B 6/4411; A61B 6/4429; A61B 6/4435; A61B 6/4447
USPC .............................. 378/19, 98.8; 250/370.09
See application file for complete search history.

(56) References Cited

U.S. PATENT DOCUMENTS

| | | | | |
|---|---|---|---|---|
| 5,487,098 A | * | 1/1996 | Dobbs .................... | A61B 6/032 378/19 |
| 5,668,851 A | * | 9/1997 | Dobbs ................... | G01T 1/1648 378/19 |
| 5,991,357 A | * | 11/1999 | Marcovici ................ | A61B 6/06 378/19 |

(Continued)

FOREIGN PATENT DOCUMENTS

| | | |
|---|---|---|
| JP | 2007-512075 A | 5/2007 |
| JP | 2014-42732 A | 3/2014 |

(Continued)

*Primary Examiner* — Allen C. Ho
(74) *Attorney, Agent, or Firm* — Oblon, McClelland, Maier & Neustadt, L.L.P.

(57) ABSTRACT

A radiation detector according to an embodiment includes a plurality of radiation detector modules and a fixing frame. When a radiation detector module is attached to the fixing frame, a guiding part with a groove shape formed at an end of a support member of the radiation detector module on a side of the fixing frame is fitted to a guiding pin provided to an end of the fixing frame, so that the radiation detector module is positioned in a radiation irradiation direction while a movement thereof in a channel direction and a row direction is restricted.

6 Claims, 8 Drawing Sheets

(56) References Cited

U.S. PATENT DOCUMENTS

| | | | |
|---|---|---|---|
| 6,396,898 B1* | 5/2002 | Saito | G01N 23/046 378/19 |
| 6,403,964 B1* | 6/2002 | Kyyhkynen | H04N 5/379 250/370.09 |
| 6,510,195 B1* | 1/2003 | Chappo | G01T 1/2018 250/208.1 |
| 6,522,715 B2* | 2/2003 | Hoffman | G01T 1/2985 250/370.11 |
| 6,587,538 B2* | 7/2003 | Igarashi | A61B 6/06 250/367 |
| 6,671,345 B2* | 12/2003 | Vrettos | A61B 6/032 378/19 |
| 6,717,150 B2* | 4/2004 | Hoffman | G01T 1/2018 250/367 |
| 6,917,664 B2* | 7/2005 | Chappo | A61B 6/032 378/15 |
| 6,925,142 B2* | 8/2005 | Pohan | A61B 6/035 250/370.15 |
| 6,982,423 B2* | 1/2006 | Elgali | G01T 1/1648 250/370.11 |
| 7,010,088 B2* | 3/2006 | Narayanaswamy | G01T 1/249 250/370.09 |
| 7,075,089 B2* | 7/2006 | Pohan | A61B 6/585 250/363.04 |
| 7,177,387 B2* | 2/2007 | Yasunaga | A61B 6/032 250/370.09 |
| 7,190,759 B2* | 3/2007 | Ratzmann | A61B 6/035 250/370.09 |
| 7,202,482 B2* | 4/2007 | Yokoi | G01T 1/2928 250/370.09 |
| 7,235,788 B2* | 6/2007 | Von der Haar | A61B 6/032 250/363.05 |
| 7,235,790 B2* | 6/2007 | Hoge | G01T 1/1648 250/370.09 |
| 7,403,589 B1* | 7/2008 | Short | A61B 6/032 250/370.11 |
| 7,433,443 B1* | 10/2008 | Tkaczyk | A61B 6/032 378/19 |
| 7,465,931 B2* | 12/2008 | Vogtmeier | A61B 6/4233 250/370.09 |
| 7,486,764 B2* | 2/2009 | Tkaczyk | G01T 1/249 250/370.09 |
| 7,489,516 B2* | 2/2009 | Lacey | A61B 6/032 250/370.08 |
| 7,492,857 B2* | 2/2009 | Yasunaga | A61B 6/032 250/370.09 |
| 7,525,097 B2* | 4/2009 | Dorscheid | G01T 1/2018 250/370.09 |
| 7,560,702 B2* | 7/2009 | Meirav | A61B 6/032 250/370.09 |
| 7,564,940 B2* | 7/2009 | Mattson | A61B 6/032 250/370.09 |
| 7,606,346 B2* | 10/2009 | Tkaczyk | A61B 6/032 250/370.09 |
| 7,606,347 B2* | 10/2009 | Tkaczyk | A61B 6/032 378/19 |
| 7,627,086 B2* | 12/2009 | Vogtmeier | G01T 1/2985 250/370.09 |
| 7,649,178 B2* | 1/2010 | Petrillo | H01M 10/425 250/370.09 |
| 7,728,298 B2* | 6/2010 | Heismann | G01T 1/166 250/363.05 |
| 7,783,000 B2* | 8/2010 | Kotooka | H01L 27/14618 378/19 |
| 7,792,239 B2* | 9/2010 | Nambu | A61B 6/4411 378/4 |
| 7,916,836 B2* | 3/2011 | Tkaczyk | G01T 1/24 378/98.8 |
| 7,956,332 B2* | 6/2011 | Burr | G01T 1/20 250/370.11 |
| 8,306,182 B2* | 11/2012 | Yaoi | A61B 6/035 378/19 |
| 8,451,977 B2* | 5/2013 | Kurochi | G01T 1/1648 378/147 |
| 8,483,352 B2* | 7/2013 | Hoffman | A61B 6/032 378/19 |
| 8,483,353 B2* | 7/2013 | Hoffman | A61B 6/032 378/19 |
| 8,483,362 B2* | 7/2013 | Freund | G21K 1/025 378/147 |
| 8,488,736 B2* | 7/2013 | Hoffman | A61B 6/482 378/19 |
| 8,525,122 B2* | 9/2013 | Chappo | A61B 6/585 250/370.11 |
| 8,536,552 B2* | 9/2013 | Freund | G01T 1/1648 250/505.1 |
| 8,548,119 B2* | 10/2013 | Ikhlef | G01T 1/2985 378/19 |
| 8,553,834 B2* | 10/2013 | Guery | A61B 6/42 378/19 |
| 8,710,448 B2* | 4/2014 | Luhta | H01L 27/14618 250/370.11 |
| 8,735,832 B2* | 5/2014 | Chappo | G01T 1/2018 250/363.01 |
| 8,772,726 B2* | 7/2014 | Herrmann | G01T 1/2018 250/361 R |
| 8,861,685 B2* | 10/2014 | Pohan | A61B 6/032 378/154 |
| 8,873,705 B2* | 10/2014 | Konno | A61B 6/032 378/19 |
| 8,890,079 B2* | 11/2014 | Kurochi | G21K 1/025 250/363.1 |
| 8,987,675 B2* | 3/2015 | Kato | A61B 6/4429 250/363.1 |
| 9,168,008 B2* | 10/2015 | Ikhlef | A61B 6/032 |
| 9,372,270 B2* | 6/2016 | Bavendiek | A61B 6/035 |
| 9,513,236 B2* | 12/2016 | Kawaguchi | G01N 23/046 |
| 9,519,069 B2* | 12/2016 | Lacey | G01T 7/005 |
| 9,986,953 B2* | 6/2018 | Nagura | A61B 6/4266 |
| 10,185,040 B2* | 1/2019 | Wirth | A61B 6/035 |
| 10,278,655 B2* | 5/2019 | Ogawa | A61B 6/4411 |
| 10,307,117 B2* | 6/2019 | Park | A61B 6/56 |
| 10,588,593 B2* | 3/2020 | Yamazaki | A61B 6/03 |
| 10,617,369 B2* | 4/2020 | Du | A61B 6/4291 |
| 10,729,392 B2* | 8/2020 | Yamamoto | A61B 6/56 |
| 10,791,999 B2* | 10/2020 | Smith | A61B 6/4225 |
| 2007/0242804 A1 | 10/2007 | Vogtmeier et al. | |
| 2014/0064443 A1 | 3/2014 | Kato | |
| 2018/0000433 A1 | 1/2018 | Yamamoto et al. | |

FOREIGN PATENT DOCUMENTS

| | | |
|---|---|---|
| JP | 2018-496 A | 1/2018 |
| JP | 2018-7971 A | 1/2018 |

* cited by examiner

RADIATION DETECTOR AND RADIATION DETECTOR MODULE

CROSS-REFERENCE TO RELATED APPLICATIONS

This application is based upon and claims the benefit of priority from Japanese Patent Application No. 2018-146698, filed on Aug. 3, 2018; the entire contents of which are incorporated herein by reference.

FIELD

Embodiments described herein relate generally to a radiation detector and a radiation detector module.

BACKGROUND

Conventionally, a medical image diagnosis apparatus that utilizes radiation, such as an X-ray computed tomography (CT) apparatus or a positron emission tomography (PET) apparatus, includes a radiation detector for detecting radiation from which projection data is generated. Some radiation detectors include a plurality of radiation detector modules, each radiation detector module being individually replaceable.

DETAILED DESCRIPTION

Figure 1:
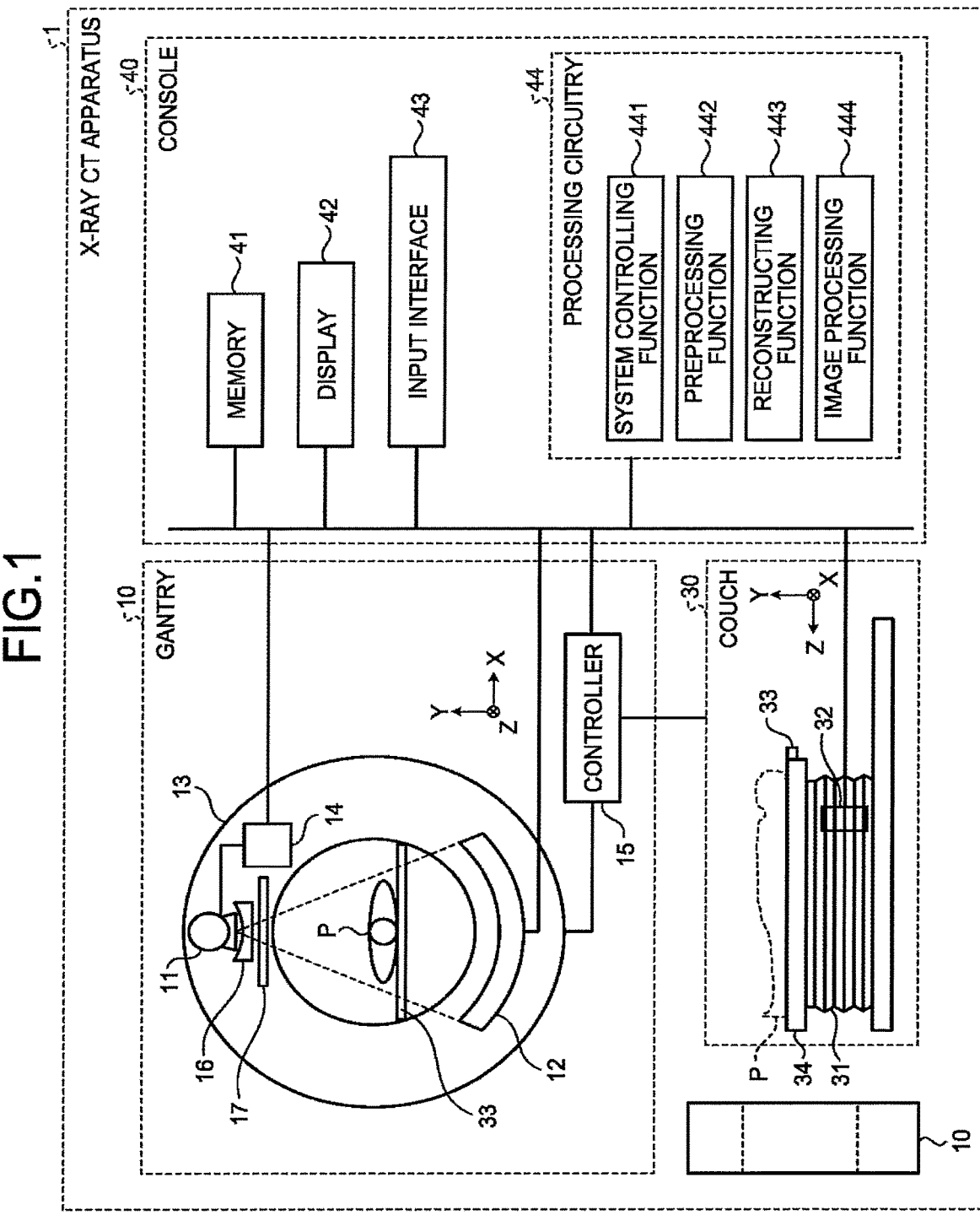
FIG. 1 is a diagram illustrating a structure example of an X-ray CT apparatus according to an embodiment.

A radiation detector according to an embodiment includes a plurality of radiation detector modules and a fixing frame. The radiation detector modules each include a detection surface where a plurality of detecting elements configured to detect radiation are arranged in a channel direction and a row direction, and a support member configured to support the detecting elements. The fixing frame is configured to fix a position of each of the radiation detector modules so that the radiation detector modules are arranged in the channel direction and attached and the detection surfaces of the radiation detector modules are arranged in the channel direction. A guiding pin is provided at an end of the fixing frame in the row direction, the guiding pin extending in a radiation irradiation direction. A guiding part with a groove shape is formed at an end of the support member on a side of the fixing frame in the row direction, the guiding part extending in the radiation irradiation direction. When the radiation detector module is attached to the fixing frame, the guiding part is fitted to the guiding pin so that the radiation detector module is positioned in the radiation irradiation direction while a movement thereof in the channel direction and the row direction is restricted.

One embodiment of a radiation detector and a radiation detector module is described with reference to the drawings. The structure illustrated in each drawing is schematic and the size of each element or the size ratio between the elements in the drawing may be different from the actual ones. Between the drawings, the size of the same element or the size ratio between the elements may be different.

The embodiment below describes an example in which the radiation detector and the radiation detector module according to the present disclosure are used in an X-ray CT apparatus.

FIG. 1 is a diagram illustrating a structure example of the X-ray CT apparatus according to the embodiment.

For example, as illustrated in FIG. 1, an X-ray CT apparatus 1 according to the present embodiment includes a gantry 10, a couch 30, and a console 40. For the convenience of the description, FIG. 1 illustrates a plurality of gantries 10.

In the present embodiment, a longitudinal direction of a rotation axis of a rotary frame 13 in a non-tilt state or a couch top 33 of the couch 30 is defined as "Z-axis direction". In addition, an axial direction that is orthogonal to the Z-axis direction and is parallel to a floor surface is defined as "X-axis direction". Furthermore, an axial direction that is orthogonal to the Z-axis direction and is perpendicular to the floor surface is defined as "Y-axis direction".

The gantry 10 irradiates a subject P (patient, for example) with an X-ray, detects the X-ray having transmitted through the subject P, and outputs the detected X-ray to the console 40. The gantry 10 includes an X-ray tube 11, an X-ray detector 12, the rotary frame 13, a controller 15, a wedge 16, an X-ray diaphragm 17, and an X-ray high-voltage device 14.

The X-ray tube 11 is a vacuum tube that generates an X-ray by delivering thermions from a cathode (filament) to an anode (target) with the application of high voltage from the X-ray high-voltage device 14. For example, the X-ray tube 11 is an X-ray tube of a rotation anode type, which generates the X-ray by delivering thermions to the rotating anode.

The wedge 16 is a filter that regulates the amount of X-ray emitted from the X-ray tube 11. Specifically, the wedge 16 is a filter that transmits and attenuates the X-ray from the X-ray tube 11 so that the X-ray to be emitted from the X-ray tube 11 to the subject P has a predetermined distribution. One example of the wedge 16 is a filter formed by processing aluminum so as to have a predetermined target angle or a predetermined thickness. Note that the wedge 16 is called a wedge filter or a bow-tie filter.

The X-ray diaphragm 17 includes a lead plate or the like to narrow down the irradiation range of the X-ray that has transmitted through the wedge 16, and by combining a plurality of lead plates or the like, a slit is formed.

The X-ray detector 12 detects the X-ray that has been emitted from the X-ray tube 11 and transmitted through the subject P. Specifically, the X-ray detector 12 includes a plurality of detecting element rows where the detecting elements are arranged in the channel direction along one arc around a focal point of the X-ray tube 11. For example, the X-ray detector 12 has a structure in which a plurality of detecting element rows, each row having the detecting elements arranged in the channel direction, are arranged in a row direction (also referred to as a slice direction).

For example, the X-ray detector 12 is an indirect conversion type detector including a collimator, a scintillator array, and an optical sensor array. The scintillator array includes a plurality of scintillators, each scintillator including a scintillator crystal that outputs light with the photon quantity corresponding to the incident X-ray quantity. The collimator (also referred to as grid) is disposed on a surface of the scintillator array on the X-ray incidence side, and includes an X-ray blocking plate that absorbs the scattering X-ray. For example, the collimator is a one-dimensional collimator or a two-dimensional collimator. The optical sensor array includes a plurality of optical sensors, each optical sensor outputting an electric signal based on the amount of light output from the corresponding scintillator. For example, the optical sensor array includes another optical sensor such as a photomultiplier tube (PMT). Note that the X-ray detector 12 may be a direct conversion type detector including a semiconductor element that converts the incident X-ray into an electric signal.

The X-ray detector 12 includes a data acquisition system (DAS) that processes the electric signal output from each detecting element. The DAS includes an amplifier that amplifies the electric signal output from each detecting element of the X-ray detector 12, and an A/D converter that converts the electric signal into a digital signal, and generates detection data. The detection data generated by the DAS is transferred to the console 40.

The X-ray high-voltage device 14 includes electric circuits such as a transformer (trans) and a rectifier, and also includes a high-voltage generator with a function of generating the high-voltage to be applied to the X-ray tube 11 and an X-ray controller that controls the output voltage based on the output of the X-ray emitted from the X-ray tube 11. The high-voltage generator may be a transformer type or an inverter type. Note that the X-ray high-voltage device 14 may be provided to the rotary frame 13 to be described below, or to a support frame (not shown) that rotatably supports the rotary frame 13 in the gantry 10.

The rotary frame 13 is an annular frame that supports the X-ray tube 11 and the X-ray detector 12, which are provided to face each other, and rotates the X-ray tube 11 and the X-ray detector 12 by the use of the controller 15 to be described below. The rotary frame 13 includes and supports the X-ray high-voltage device 14 in addition to the X-ray tube 11 and the X-ray detector 12. The detection data generated by the DAS in the X-ray detector 12 is transmitted from a transmitter including a light-emitting diode (LED) provided to the rotary frame 13, to a receiver including a photodiode provided to a non-rotary part of the gantry 10 (for example, support frame) through optical communication, and transferred to the console 40. A method of transmitting the detection data from the rotary frame 13 to the non-rotary part of the gantry 10 is not limited to the aforementioned optical communication and may be any method that enables the non-contact data transmission.

The controller 15 includes a processing circuitry including a central processing unit (CPU) or the like, and a driving mechanism such as a motor and an actuator. The controller 15 includes a function of controlling the operation of the gantry 10 and the couch 30 upon receiving an input signal from an input interface 43 attached to the console 40 or the gantry 10. For example, upon receiving the input signal, the controller 15 controls to rotate the rotary frame 13, tilt the gantry 10, or operate the couch 30 and the couch top 33. Note that the control of tilting the gantry 10 is performed by causing the controller 15 to rotate the rotary frame 13 around an axis parallel to the X-axis direction on the basis of the inclination angle (tilt angle) information input from the input interface 43 provided to the gantry 10. Note that the controller 15 may be provided to the gantry 10 or the console 40.

The couch 30 is a device on which the subject P to be scanned is mounted and moved, and includes a base 31, a couch driving device 32, the couch top 33, and a support frame 34. The base 31 is a housing that supports the support frame 34 in a manner that the support frame 34 can be moved in the vertical direction. The couch driving device 32 is a motor or an actuator that moves the couch top 33 with the subject P mounted thereon in a major-axis direction of the couch top 33. The couch top 33 provided to an upper surface of the support frame 34 is a plate on which the subject P is mounted. The couch driving device 32 may move, in addition to the couch top 33, the support frame 34 in the major-axis direction of the couch top 33.

The console 40 is a device that receives the operator's operation of the X-ray CT apparatus 1 and reconstructs the CT image data using the detection data collected by the gantry 10. The console 40 includes a memory 41, a display 42, the input interface 43, and a processing circuitry 44. In the example described here, the console 40 and the gantry 10 are separate bodies; however, the gantry 10 may include the console 40 or a part of the console 40.

The memory 41 is formed by, for example, a semiconductor memory element such as a random access memory (RAM) or a flash memory, a hard disk, an optical disk, or the like. The memory 41 stores the projection data or the CT image data, for example.

The display 42 displays various kinds of information. For example, the display 42 outputs medical images (CT images) generated by the processing circuitry 44, a graphical user interface (GUI) for receiving various operations from the operator, and the like. The display 42 is, for example, a liquid crystal display or a cathode ray tube (CRT) display. The display 42 may be provided to the gantry 10, for example. In another example, the display 42 may be a desktop type or formed as a tablet terminal that can communicate wirelessly with the main body of the console 40.

The input interface 43 receives various input operations from the operator, converts the received input operation into electric signals, and outputs the signals to the processing circuitry 44. For example, the input interface 43 receives, from the operator, a collecting condition when collecting the projection data, a reconstructing condition when reconstructing the CT image data, an image processing condition when generating a processed image from the CT image, and the like. For example, the input interface 43 is formed by a mouse, a keyboard, a track ball, a switch, a button, a joystick, or the like. For example, the input interface 43 may be provided to the gantry 10 or formed as a tablet terminal or the like that can communicate wirelessly with the main body of the console 40.

The processing circuitry 44 controls the entire operation of the X-ray CT apparatus 1. For example, the processing circuitry 44 performs a system controlling function 441, a preprocessing function 442, a reconstructing function 443, and an image processing function 444.

The system controlling function 441 controls various functions of the processing circuitry 44 on the basis of the input operation received from the operator through the input interface 43. For example, the system controlling function 441 controls the CT scan performed in the X-ray CT apparatus 1. The system controlling function 441 controls the preprocessing function 442, the reconstructing function 443, and the image processing function 444, so as to control the generation or display of the CT image data in the console 40.

The preprocessing function 442 performs the preprocessing such as a logarithmic transformation process, an offset correction process, an inter-channel sensitivity correction process, or a beam hardening correction, on the detection data output from the DAS of the X-ray detector 12, and generates the preprocessed projection data. The data (detection data) before the preprocessing and the data after the preprocessing may be collectively referred to as the projection data.

The reconstructing function 443 performs a reconstructing process using a filtered back projection, a successive approximation reconstruction, or the like, on the projection data generated in the preprocessing function 442, and generates the CT image data (reconstructed image data).

The image processing function 444 converts the CT image data, which have been generated by the reconstructing function 443, into tomographic data along an arbitrary cross section or three-dimensional image data by a known method on the basis of the input operation received from the operator through the input interface 43. Note that the three-dimensional image data may be directly generated by the reconstructing function 443.

Here, for example, the processing circuitry 44 is achieved by the processor. In this case, the processing functions in the processing circuitry 44 are stored in the memory 41 in the form of computer programs that can be performed by a computer. By reading and executing each computer program in the memory 41, the processing circuitry 44 achieves the function corresponding to that computer program. In other words, the processing circuitry 44 that has read out the computer program has the processing function of the processing circuitry 44 illustrated in FIG. 1.

Here, each processing function is achieved by one processing circuitry 44; however, the processing circuitry 44 may be formed by combining a plurality of independent processors and each processing function may be achieved by causing each processor to execute the computer program. Each processing function of the processing circuitry 44 may be achieved dispersedly or integrally in one or a plurality of process circuitries. In addition, each processing function of the processing circuitry 44 may be achieved by mixing hardware such as circuitry and software. In this example, one memory 41 stores the computer program corresponding to each processing function; however, the embodiment is not limited to this example. For example, a plurality of storage circuitries may be dispersedly disposed and the processing circuitry 44 may read out the corresponding computer program from the individual storage circuitry and executes the computer program.

The overall structure of the X-ray CT apparatus 1 according to the present embodiment has been described. In this structure, the X-ray detector 12 in the X-ray CT apparatus 1 according to the present embodiment includes the X-ray detector modules and each X-ray detector module is independently replaceable. In such a structure, for example, in the occurrence of the abnormality in the X-ray detector 12, the X-ray detector module with the abnormality can be replaced independently; therefore, the downtime of the system can be shortened.

Figure 2:
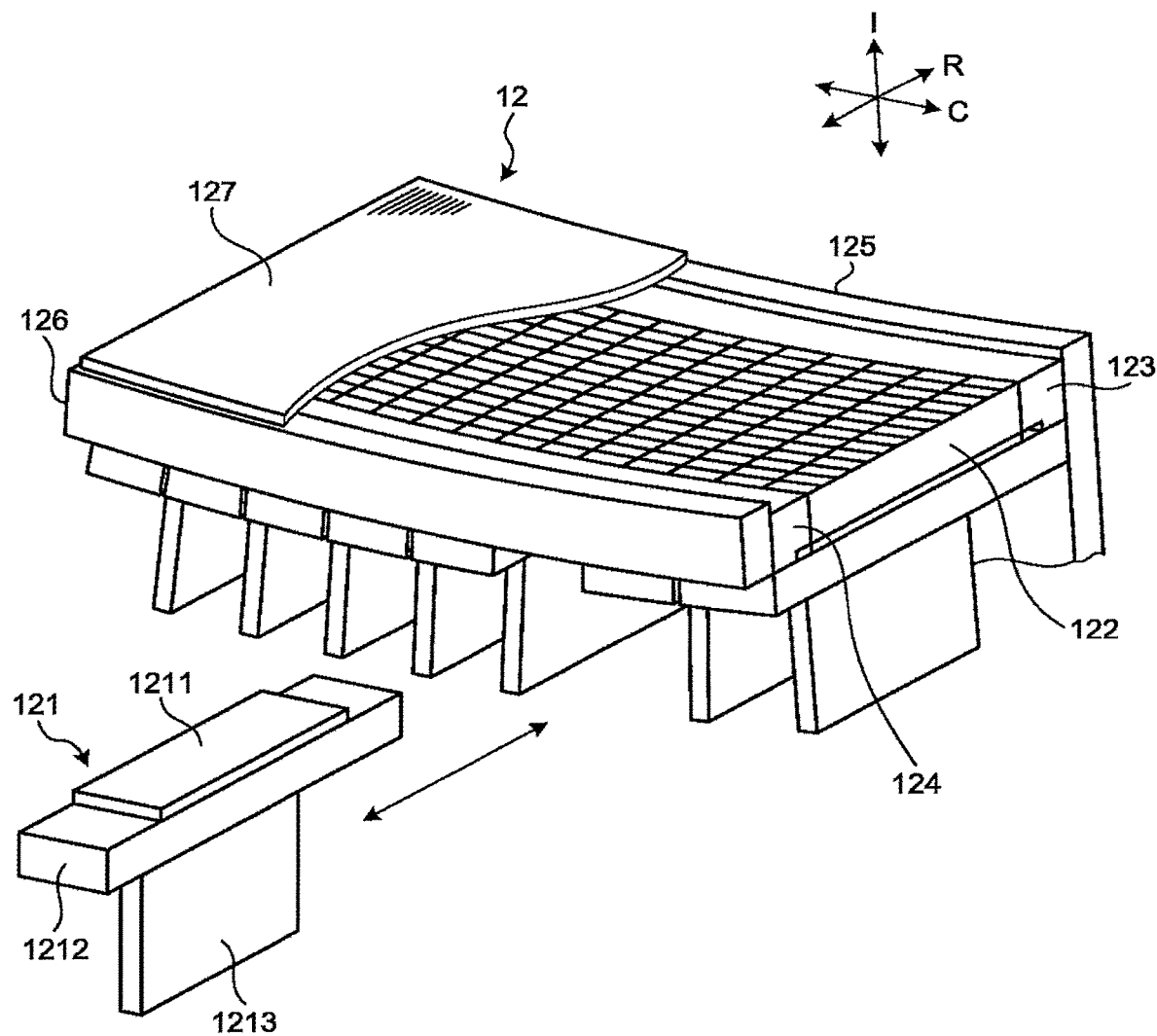
FIG. 2 is a diagram illustrating a structure example of an X-ray detector according to an embodiment.

FIG. 2 is a diagram illustrating a structure example of the X-ray detector 12 according to the present embodiment.

For example, as illustrated in FIG. 2, the X-ray detector 12 according to the present embodiment has an approximately arc-like shape as a whole, with a center of the arc being fixed to the rotary frame 13 so as to coincide with the position of the X-ray tube 11. Here, the circumferential direction of the arc in the X-ray detector 12 coincides with the channel direction. In addition, the axial direction of the arc in the X-ray detector 12 coincides with the row direction. Furthermore, the radial direction of the arc in the X-ray detector 12 coincides with an X-ray irradiation direction. In each drawing referred to in the description below, the channel direction is indicated by an arrow C, the row direction is indicated by an arrow R, and the X-ray irradiation direction is indicated by an arrow I.

Specifically, the X-ray detector 12 includes a plurality of X-ray detector modules 121, a collimator 122, a first fixing frame 123, a second fixing frame 124, a first support frame 125, a second support frame 126, and a light-blocking plate 127. The X-ray detector 12 is one example of radiation detectors.

The X-ray detector module 121 includes a detection surface 1211, a support member 1212, and a DAS 1213. Note that the X-ray detector module 121 is one example of radiation detector modules.

The detection surface 1211 is formed by having the detecting elements for detecting the X-ray arranged in the channel direction and the row direction. Specifically, the detection surface 1211 is formed by having the detecting element rows, each having the detecting elements arranged in the channel direction, arranged in the row direction.

The support member 1212 supports the X-ray elements that form the detection surface 1211. Specifically, the support member 1212 is formed to have an approximately rectangular parallelepiped shape, and on a surface of the support member 1212 that faces the X-ray tube 11, the detection surface 1211 is fixed.

The DAS 1213 includes an amplifier that amplifies the electric signal output from each detecting element in the X-ray detector 12, and an A/D converter that converts the electric signal into a digital signal, and generates the detection data. Specifically, the DAS 1213 is structured as a board having the amplifier and the A/D mounted thereon, and is attached to the surface of the support member 1212 that is opposite to the detection surface 1211 so as to extend along the X-ray irradiation direction.

The collimator 122 is formed by having a plurality of collimator plates disposed in a lattice form, and removes the scattering ray from the X-ray that enters each X-ray detector module 121. Specifically, the collimator 122 is formed to have an approximately arc-like shape along the channel direction, and is disposed to cover the detection surface 1211 of the X-ray detector module 121.

The first fixing frame 123 and the second fixing frame 124 fix the positions of the X-ray detector modules 121 so that the X-ray detector modules 121 are arranged in the channel direction and attached and the detection surfaces 1211 of the X-ray detector modules 121 are arranged in the channel direction.

Specifically, the first fixing frame 123 is fixed at one end in the row direction of the collimator 122, and the second fixing frame 124 is fixed at the other end in the row direction of the collimator 122. To the first fixing frame 123 and the second fixing frame 124, the X-ray detector modules 121 that are arranged in the channel direction are attached along the surface of the collimator 122 that is opposite to the surface thereof facing the X-ray tube 11. In the description below, the first fixing frame 123 and the second fixing frame 124 are collectively referred to as the fixing frame unless they need to be distinguished.

The first support frame 125 and the second support frame 126 support the collimator 122 and the fixing frames. Specifically, the first support frame 125 and the second support frame 126 support the collimator 122 and the fixing frames so as to hold them from both sides in the row direction, and in this state, the first support frame 125 and the second support frame 126 are fixed to the support frame (not shown) of the gantry 10.

The light-blocking plate 127 reduces the amount of light entering the detection surface 1211 of each X-ray detector module 121. For example, the light-blocking plate 127 is a member formed of a material that can suppress the light and has a shape like a thin plate. The light-blocking plate 127 is attached to the first support frame 125 and the second support frame 126 so as to cover the entire collimator 122.

The X-ray detector 12 according to the present embodiment is configured so that each X-ray detector module 121 is independently detachable from the fixing frame with the other adjacent X-ray detector modules 121 left attached.

When the X-ray detector module 121 is detached with the other adjacent X-ray detector modules 121 left attached, the X-ray detector module 121 to be detached may interfere with the attached X-ray detector module 121. Therefore, a worker needs to perform the exchanging operation carefully.

In view of the above, the X-ray detector 12 according to the present embodiment is configured to enable the worker to exchange the X-ray detector module 121 more easily.

Specifically, in the present embodiment, when the X-ray detector module 121 is attached to the fixing frame, the X-ray detector module 121 is positioned in the X-ray irradiation direction while the movement thereof in the channel direction and the row direction is restricted.

Figure 3:
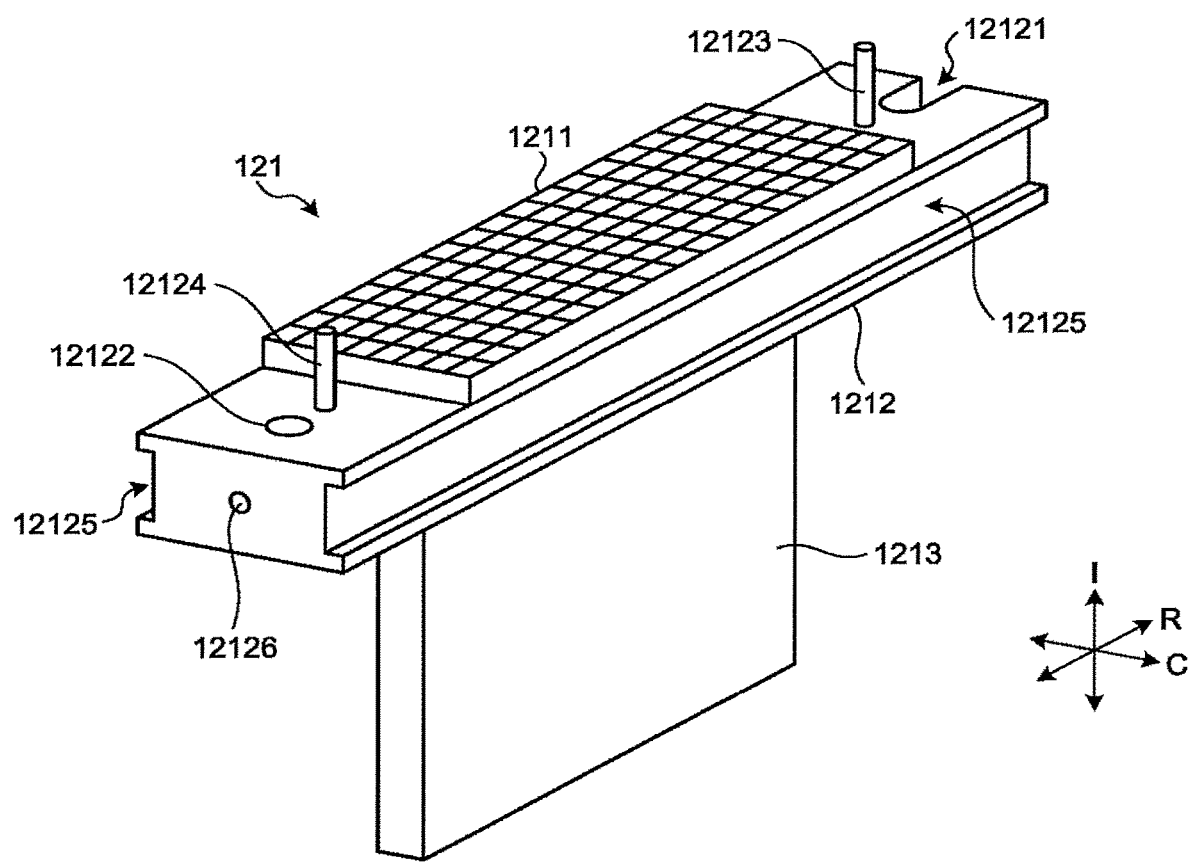
FIG. 3 is a diagram illustrating a structure example of an X-ray detector module according to an embodiment.
Figure 4:
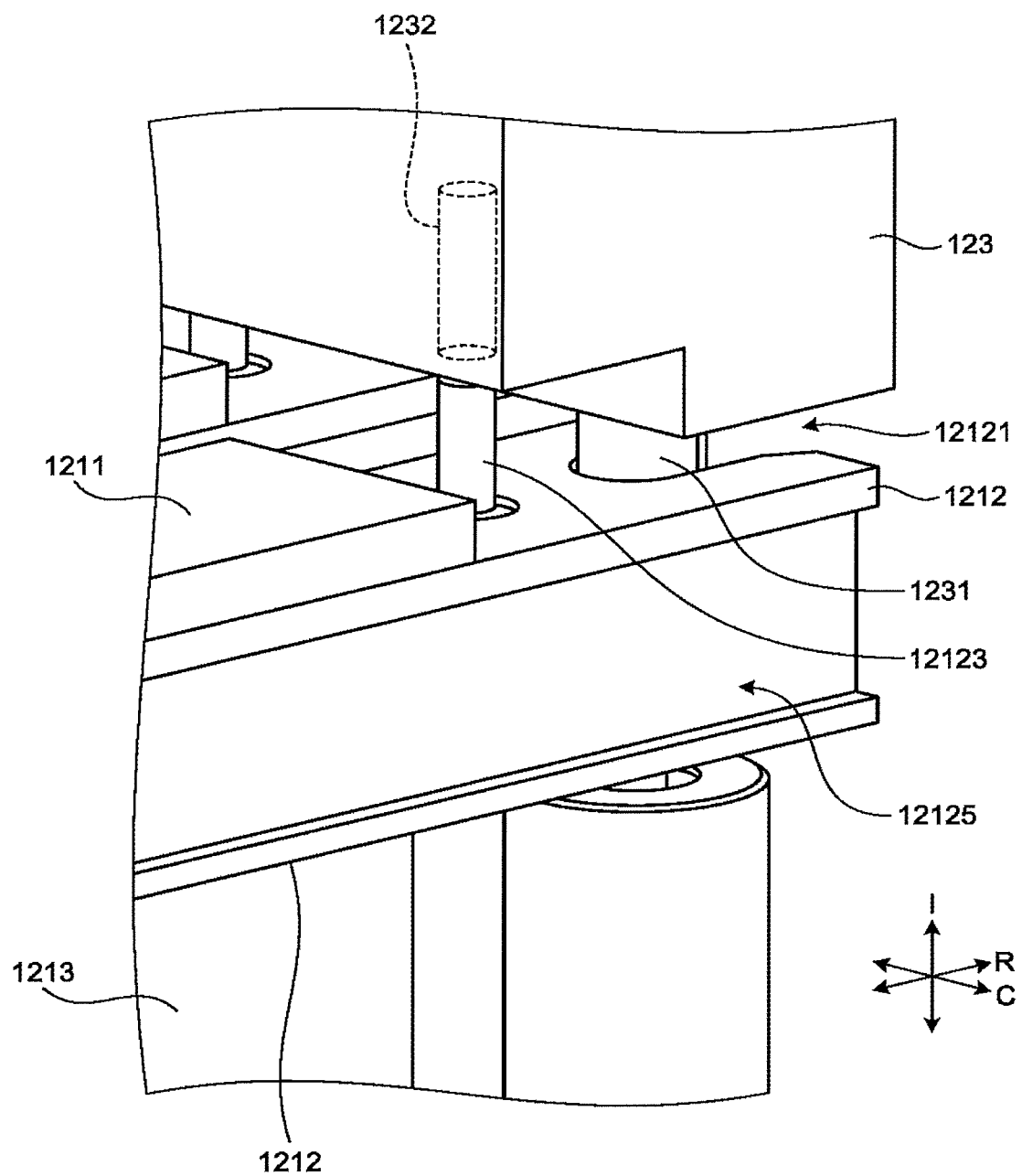
FIG. 4 is a diagram illustrating a structure example of a first fixing frame according to an embodiment.

FIG. 3 is a diagram illustrating a structure example of the X-ray detector module 121 according to the present embodiment. FIG. 4 is a diagram illustrating a structure example of the first fixing frame 123 according to the present embodiment.

For example, as illustrated in FIG. 3, the support member 1212 of the X-ray detector module 121 includes a guiding part 12121, a fixing hole 12122, a first positioning pin 12123, a second positioning pin 12124, a guidance groove 12125, and a jig fixing hole 12126.

The guiding part 12121 is formed at one end of the support member 1212 in the row direction and has a groove shape that extends in the X-ray irradiation direction. Specifically, at one end of the support member 1212 in the row direction, the guiding part 12121 is provided at an approximately central position in the channel direction and is formed to have a cross section, which is orthogonal to the X-ray irradiation direction, that is like a letter U. Here, the guiding part 12121 is provided to the support member 1212 at the end that, when the X-ray detector module 121 is attached to the first fixing frame 123 and the second fixing frame 124, comes to the first fixing frame side.

The fixing hole 12122 is provided at the other end of the support member 1212 in the row direction, and is formed so as to penetrate the support member 1212 in the X-ray irradiation direction. Specifically, the fixing hole 12122 is provided at an approximately central position in the channel direction at the end of the support member 1212 that is opposite to the end where the guiding part 12121 is provided in the row direction.

The first positioning pin 12123 is provided to the surface of the support member 1212 on the side that faces the first fixing frame 123, and is formed to project in the X-ray irradiation direction. Specifically, the first positioning pin 12123 is formed to have a long and thin stick shape, and is provided to project from between the detection surface 1211 and the guiding part 12121 on the surface of the support member 1212 on the side that faces the first fixing frame 123.

The second positioning pin 12124 is provided to the surface of the support member 1212 on the side that faces the second fixing frame 124, and is formed to project in the X-ray irradiation direction. Specifically, the second positioning pin 12124 is formed to have a long and thin stick shape similar to the first positioning pin 12123, and is provided to project from between the detection surface 1211 and the fixing hole 12122 on the surface of the support member 1212 on the side that faces the first fixing frame 123.

The guidance groove 12125 is provided to each side surface of the support member 1212 in the channel direction and is formed to extend in the row direction. Specifically, the guidance groove 12125 is formed to have a planar bottom surface and have uniform width in the X-ray irradiation direction along the entire length in the row direction in each surface of the support member 1212 in the channel direction.

The jig fixing hole 12126 is provided to an end surface of the support member 1212 that is opposite to the guiding part 12121 in the row direction, and includes a screw formed on the inside. Specifically, the jig fixing hole 12126 is provided at an approximately central position in the X-ray irradiation direction and in the channel direction on the end surface of the support member 1212 that is opposite to the guiding part 12121 in the row direction.

On the other hand, for example, as illustrated in FIG. 4, the first fixing frame 123 includes a guiding pin 1231 and a positioning hole 1232 in the present embodiment.

The guiding pin 1231 is provided at the end of the first fixing frame 123 in the row direction so as to extend in the X-ray irradiation direction. Specifically, the guiding pin 1231 is a stick-shaped member whose cross-sectional shape that is orthogonal to the longitudinal direction is circular. The guiding pin 1231 has one end fixed while being inserted in the hole of the first fixing frame 123, and the other end extending in the X-ray irradiation direction from the surface of the first fixing frame 123 on the side that faces the X-ray detector module 121.

The positioning hole 1232 is provided to the surface of the first fixing frame 123 on the side that faces the support member 1212 of the X-ray detector module 121, and is formed to extend in the X-ray irradiation direction. Specifically, the positioning hole 1232 is a hole to position the X-ray detector module 121 at an attachment position that is determined in advance with respect to the first fixing frame 123 in the channel direction and the row direction. The positioning hole 1232 is formed at the position where the first positioning pin 12123 of the X-ray detector module 121 is to be disposed when the X-ray detector module 121 is disposed at that attachment position.

Although not shown in FIG. 4, the second fixing frame 124 also includes a positioning hole that extends in the X-ray irradiation direction on the surface on the side that faces the support member 1212 of the X-ray detector module 121. Specifically, the positioning hole, which extends in the X-ray irradiation direction, is formed at the position where the second positioning pin 12124 of the X-ray detector module 121 is to be disposed when the X-ray detector module 121 is disposed at that attachment position.

In the present embodiment, when the X-ray detector module 121 is attached to the fixing frame, the aforementioned structure causes the guiding part 12121 of the support member 1212 to be fitted to the guiding pin 1231 of the first fixing frame 123; therefore, the X-ray detector module 121 can be positioned in the radiation irradiation direction while the movement thereof in the channel direction and the row direction is restricted.

Then, in the present embodiment, when the X-ray detector module 121 is attached to the fixing frame, the aforementioned structure causes the first positioning pin 12123 to be fitted to the positioning hole 1232 of the first fixing frame 123 and the second positioning pin 12124 to be fitted to the positioning hole of the second fixing frame 124 with the guiding part 12121 of the support member 1212 fitted to the guiding pin 1231; thus, the position in the channel direction and the row direction is fixed.

Here, for example, the groove width of the guiding part 12121 of the support member 1212 in the channel direction is larger than the width of the guiding pin 1231 of the first fixing frame 123 in the channel direction, and the difference from the width of the guiding pin 1231 in the channel direction is smaller than the gap from the adjacent X-ray detector module 121 that is attached to the first fixing frame 123.

That is to say, in the present embodiment, the groove width of the guiding part 12121 provided to the support member 1212 may be different from the width of the guiding pin 1231 of the first fixing frame 123 in the channel direction, and may be larger than the width of the guiding pin 1231 within the range not interfering with the adjacent X-ray detector module 121. In this case, the X-ray detector module 121 with the guiding part 12121 fitted to the guiding pin 1231 can move in the channel direction within the range not interfering with the adjacent X-ray detector module 121.

Thus, for example, when attaching the X-ray detector module 121 to the fixing frame, the worker first fits the guiding part 12121 to the guiding pin 1231 of the first fixing frame 123 to roughly check the attachment position of the X-ray detector module 121, and then, fits the positioning pin to the positioning hole of the fixing frame while minutely adjusting the position of the X-ray detector module 121; thus, the X-ray detector module 121 can be attached in the end.

Furthermore, in the present embodiment, when the X-ray detector module 121 is attached to the fixing frame, the guidance groove 12125 of the support member 1212 is slidably supported by the jig provided to the guidance groove 12125 of the support member 1212 of another attached X-ray detector module 121; thus, the X-ray detector module 121 is guided to move to the X-ray irradiation direction to approach obliquely the fixing frame.

Figure 5:
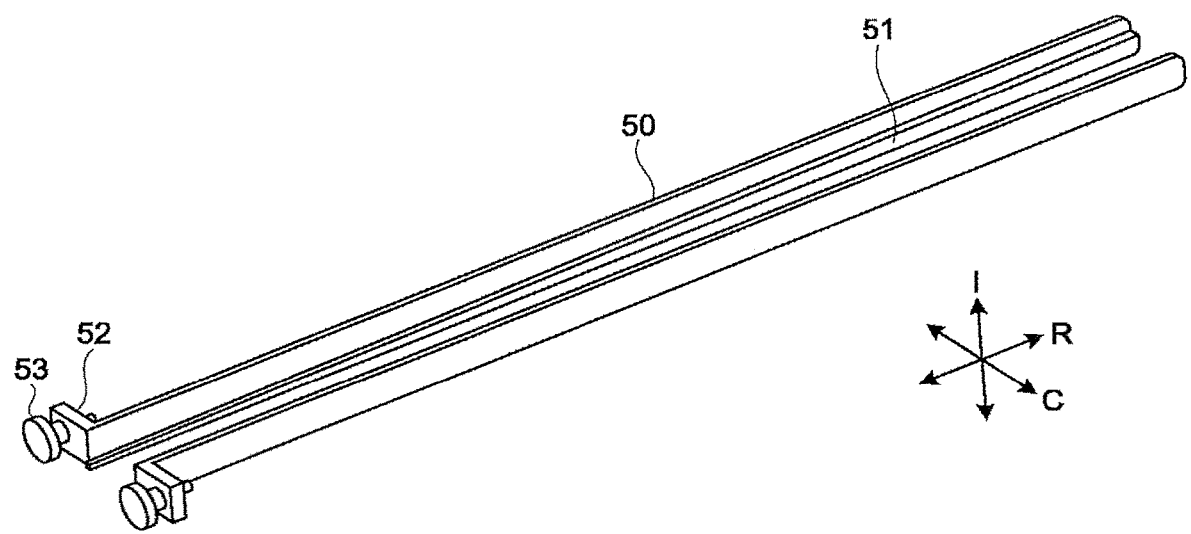
FIG. 5 is a diagram illustrating a structure example of a jig according to an embodiment.

FIG. 5 is a diagram illustrating a structure example of the jig according to the present embodiment.

For example, as illustrated in FIG. 5, a jig 50 has a stick-like shape, and includes a guidance part 51, an attachment part 52, and an attachment screw 53.

The guidance part 51 is formed to project in the channel direction from the support member 1212 when the jig 50 is attached to the guidance groove 12125 of the support member 1212 of the X-ray detector module 121 along the approximately entire length of the jig 50. The guidance part 51 includes an inclined surface that is formed to approach the first fixing frame 123 in the X-ray irradiation direction from the end disposed opposite to the guiding part 12121 in the row direction to the end disposed on the guiding part 12121 side when the jig 50 is attached to the guidance groove 12125 of the support member 1212 of the X-ray detector module 121.

The attachment part 52 is provided at the end disposed opposite to the guiding part 12121 in the row direction when the jig 50 is attached to the guidance groove 12125 of the support member 1212 of the X-ray detector module 121, and formed to extend from the end to the position of the jig fixing hole 12126 of the support member 1212.

The attachment screw 53 is rotatably attached to an end of the attachment part 52, and by the engagement of the jig 50 with the jig fixing hole 12126 with the jig 50 fitted to the guidance groove 12125 of the support member 1212 of the X-ray detector module 121, the jig 50 is fixed to the support member 1212.

In the present embodiment, when the X-ray detector module 121 is attached to the fixing frame, the aforementioned structure causes the guidance groove 12125 of the support member 1212 to be moved in the row direction in sliding contact with the inclined surface of the guidance part 51 of the jig 50 attached to the guidance groove 12125 of the support member 1212 of the other attached radiation detector module; thus, the X-ray detector module 121 is guided to move to the X-ray irradiation direction so as to approach the fixing frame obliquely.

Figure 6:
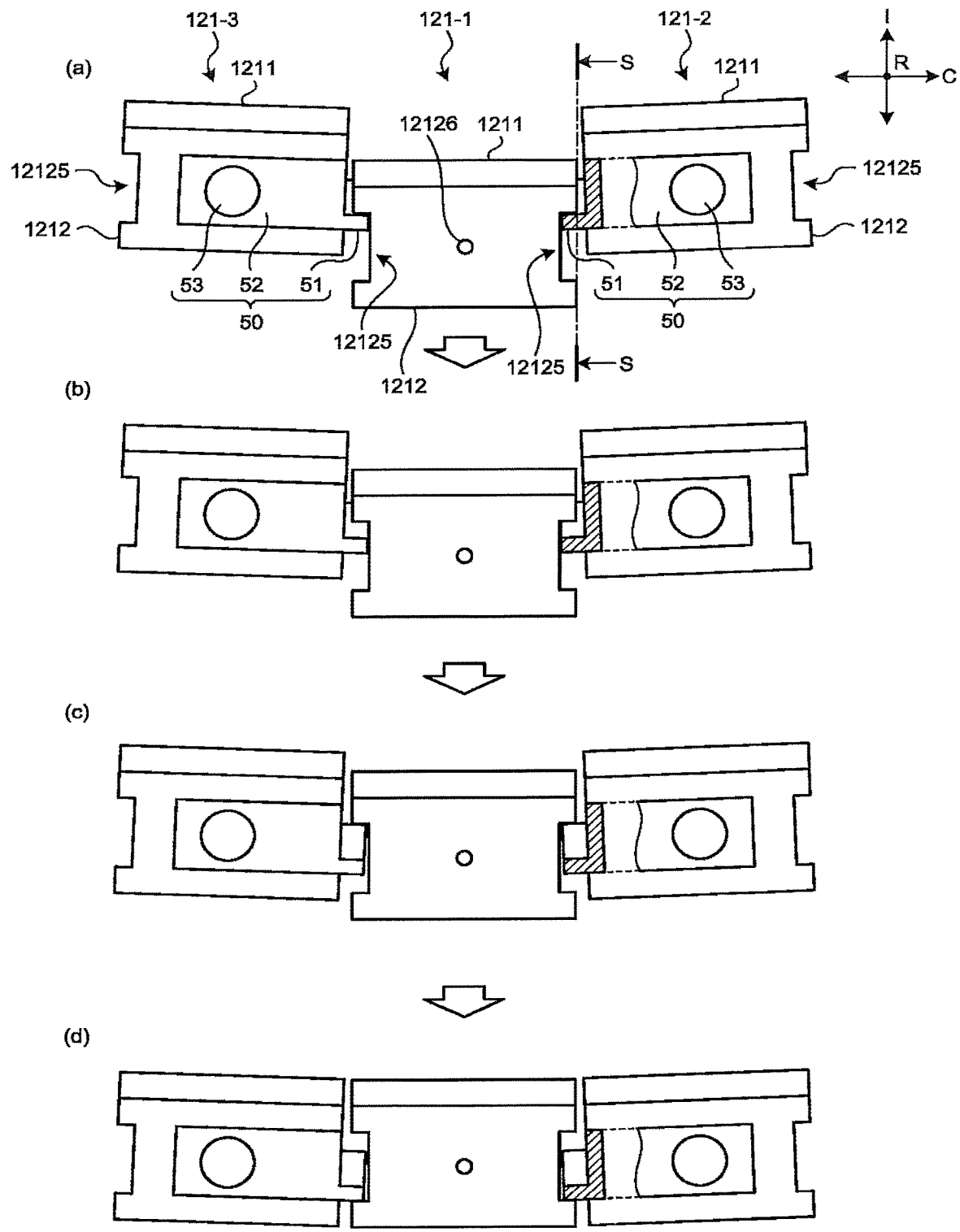
FIG. 6 is a diagram illustrating how the X-ray detector module according to an embodiment is attached.
Figure 7:
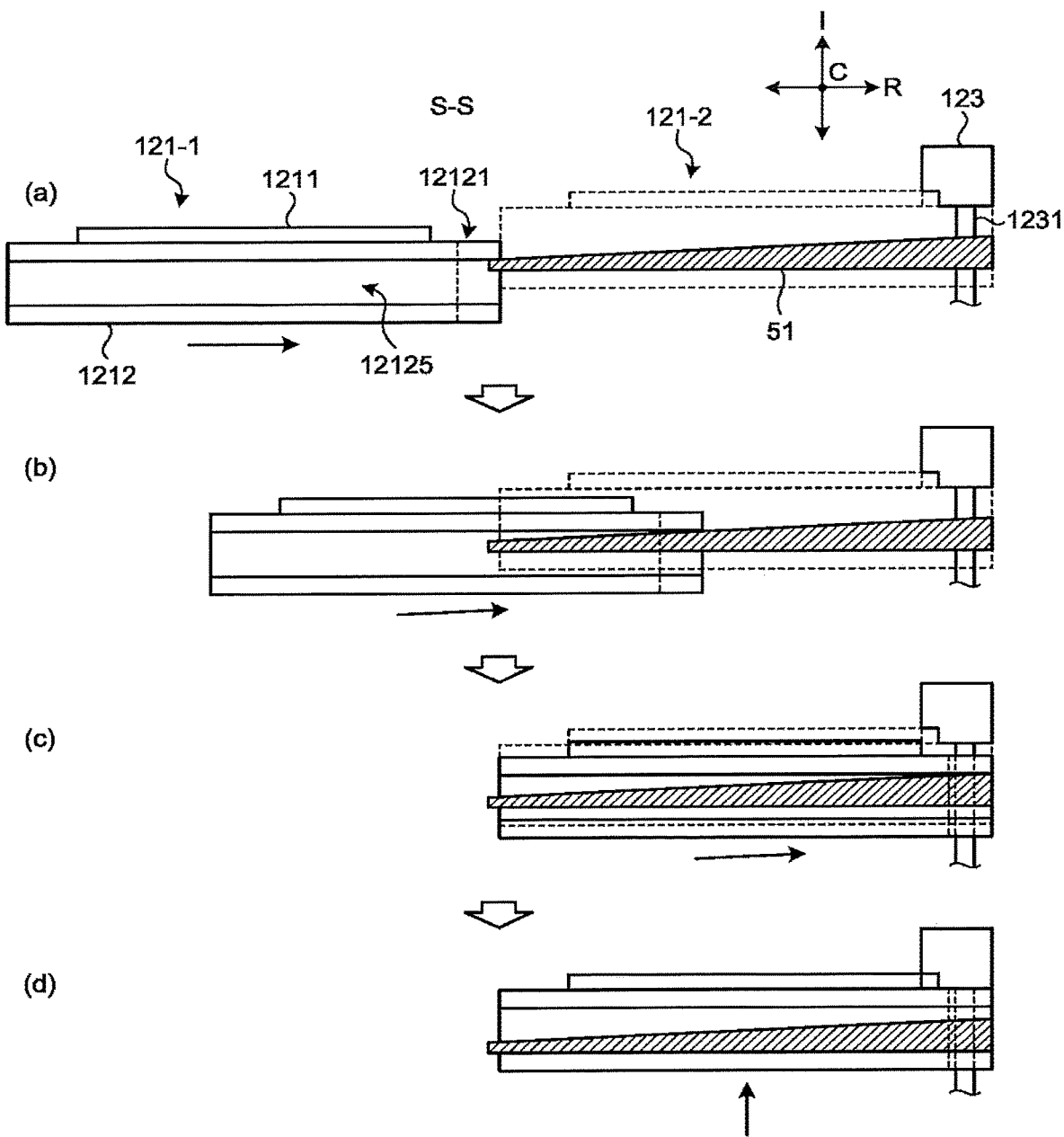
FIG. 7 is a diagram illustrating how the X-ray detector module according to an embodiment is attached.

FIGS. 6 and 7 are diagrams illustrating how the X-ray detector module 121 according to the present embodiment is attached.

Here, FIGS. 6 and 7 illustrate the three X-ray detector modules 121 that are provided adjacent to each other in the X-ray detector 12. FIG. 6 is a front view in which each X-ray detector module 121 is viewed in the row direction. FIG. 7 is a side view in which each X-ray detector module 121 is viewed in the channel direction and each include the cross section along line S-S in FIG. 6. Note that FIGS. 6 and 7 do not illustrate the DAS 1213 of each X-ray detector module 121.

In the example in FIGS. 6 and 7, a first X-ray detector module 121-1 at the center is to be attached, and a second X-ray detector module 121-2 and a third X-ray detector module 121-3 on both sides are already attached to the fixing frame.

In this case, for each of the second X-ray detector module 121-2 and the third X-ray detector module 121-3 that are already attached to the fixing frame, the jig 50 is attached to the guidance groove 12125 on the side where the first X-ray detector module 121-1 to be attached is disposed. Then, the jig 50 that is attached to each of the second X-ray detector module 121-2 and the third X-ray detector module 121-3 is fixed to each X-ray detector module with the attachment screw 53.

After that, as illustrated in FIG. 6(*a*) and FIG. 7(*a*), the first X-ray detector module 121-1 is inserted between the second X-ray detector module 121-2 and the third X-ray detector module 121-3 in the row direction from an end where the guiding part 12121 is provided.

Here, the first X-ray detector module 121-1 is inserted in a state where the end of the guidance groove 12125 of the support member 1212 is hung on the inclined surface of the guidance part 51 of the jig 50 attached to each of the second X-ray detector module 121-2 and the third X-ray detector module 121-3. Thus, the guidance groove 12125 of the support member 1212 of the first X-ray detector module 121-1 is slidably supported by the jig 50 that is attached to each of the second X-ray detector module 121-2 and the third X-ray detector module 121-3. That is to say, the sliding surface within the guidance groove 12125 of the support member 1212 of the first X-ray detector module 121-1 is slidably supported by the inclined surface that is provided, obliquely to the sliding surface, to the jig 50 attached to the guidance groove 12125 of the support member 1212 of each of the second X-ray detector module 121-2 and the third X-ray detector module 121-3; thus, the first X-ray detector module 121-1 is guided to move to the X-ray irradiation direction so as to approach the fixing frame obliquely.

After that, as illustrated in FIG. 6(b) and FIG. 7(b), the first X-ray detector module 121-1 is further inserted between the second X-ray detector module 121-2 and the third X-ray detector module 121-3 in the row direction.

Here, the X-ray detector module 121 is moved in the row direction with the guidance groove 12125 of the support member 1212 in sliding contact with the inclined surface of the guidance part 51 of the jig 50 attached to each of the second X-ray detector module 121-2 and the third X-ray detector module 121-3; thus, the X-ray detector module 121 is guided to move to the X-ray irradiation direction so as to approach the fixing frame obliquely.

After that, as illustrated in FIG. 6(c) and FIG. 7(c), the first X-ray detector module 121-1 is further inserted between the second X-ray detector module 121-2 and the third X-ray detector module 121-3 in the row direction until the guiding part 12121 is fitted to the guiding pin 1231 of the first fixing frame 123.

Here, by the fitting of the guiding part 12121 of the support member 1212 to the guiding pin 1231 of the first fixing frame 123, the X-ray detector module 121 is guided to move to the X-ray irradiation direction as to approach the fixing frame obliquely while the movement of the X-ray detector module 121 in the channel direction and the row direction is restricted.

After that, as illustrated in FIG. 6(d) and FIG. 7(d), the first X-ray detector module 121-1 is attached to the first fixing frame 123 after being moved toward the first fixing frame 123 in the X-ray irradiation direction.

Here, the first X-ray detector module 121-1 is pressed by a fixing member toward the first fixing frame 123 from the side opposite to the first fixing frame 123; thus, the first X-ray detector module 121-1 is moved in the X-ray irradiation direction and attached to the first fixing frame 123.

Figure 8:
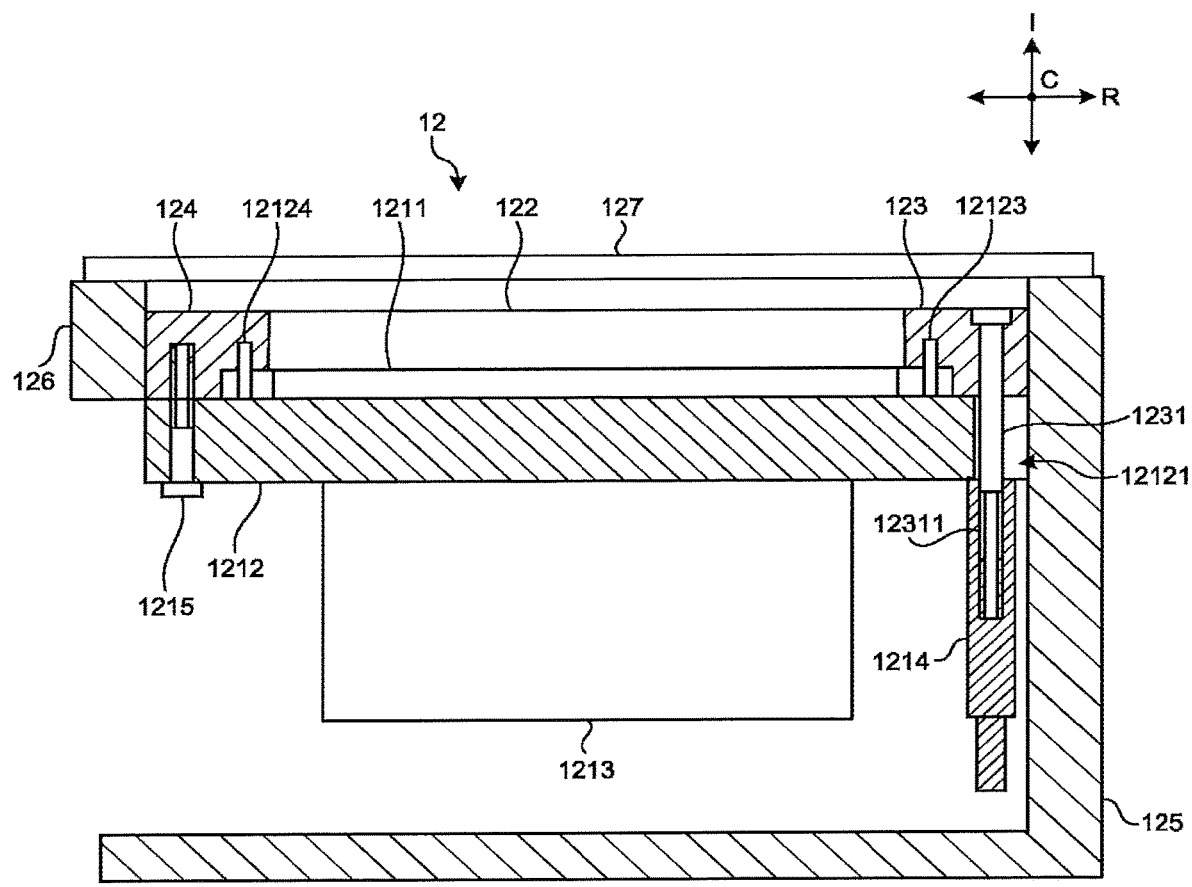
FIG. 8 is a diagram illustrating a state in which the X-ray detector module according to an embodiment is attached to the fixing frame.

FIG. 8 is a diagram illustrating the state in which the X-ray detector module 121 according to the present embodiment is attached to the fixing frame.

For example, as illustrated in FIG. 8, in the present embodiment, a screw is formed at the end of the guiding pin 1231 provided to the first fixing frame 123. With the guiding part 12121 fitted to the guiding pin 1231, the X-ray detector module 121 is pressed to the first fixing frame 123 by the fixing member 1214 provided with a screw to be engaged with the screw of the guiding pin 1231 from the side opposite to the first fixing frame 123; thus, the X-ray detector module 121 is fastened to the first fixing frame 123.

Here, for example, the fixing member 1214 is formed to be longer than the DAS 1213 when the X-ray detector module 121 is positioned relative to the first fixing frame 123 in the X-ray irradiation direction. Thus, the worker can reach for the fixing member 1214 over the DAS 1213 and can operate the fixing member 1214; thus, without the interruption by the DAS 1213, the worker can easily attach the X-ray detector module 121 to the first fixing frame 123.

In addition, in the present embodiment, the surface of the second fixing frame 124 that faces the support member 1212 of the X-ray detector module 121 includes a screw hole. On the other hand, an end of the support member 1212 of the X-ray detector module 121 that faces the second fixing frame 124 includes a penetration hole that penetrates in the X-ray irradiation direction. The X-ray detector module 121 is fastened to the second fixing frame 124 by having a screw 1215, which is screwed into the screw hole of the second fixing frame 124, inserted into the penetration hole from the side opposite to the second fixing frame 124 and causing the screw 1215 to press the X-ray detector module 121 to the second fixing frame 124.

Thus, in the present embodiment, the X-ray detector module 121, when attached to the fixing frame, has the guiding part 12121 of the support member 1212 fitted to the guiding pin 1231 of the first fixing frame 123; thus, the X-ray detector module 121 is positioned in the radiation irradiation direction while the movement thereof in the channel direction and the row direction is restricted.

In the present embodiment, the X-ray detector module 121, when attached to the fixing frame, has the guidance groove 12125 of the support member 1212 slidably supported by the jig attached to the guidance groove 12125 of the support member 1212 of the other attached X-ray detector module 121; thus, the X-ray detector module 121 is guided to move to the X-ray irradiation direction so as to approach the fixing frame obliquely.

For example, in the case where the X-ray detector module 121 is attached to the fixing frame, the X-ray detector module 121 may be inserted linearly in the row direction and moved to the X-ray irradiation direction just before the X-ray detector module 121 is attached to the fixing frame. In contrast to this structure, in the present embodiment, the X-ray detector module 121 is guided to move to the X-ray irradiation direction so as to approach the fixing frame obliquely; therefore, moving the X-ray detector module 121 to the X-ray irradiation direction just before the X-ray detector module 121 is attached to the fixing frame requires a shorter distance. Thus, the risk of the interference between the X-ray detector module to be attached and the attached X-ray detector module 121 can be reduced more.

In addition, in the present embodiment, the X-ray detector module 121 is attached and fixed to the fixing frame that is fixed to the collimator 122; therefore, the X-ray detector module 121 can be positioned more accurately to the collimator 122.

Thus, according to the present embodiment, the worker can perform the operation more easily in attaching the X-ray detector module 121.

In the above description, mainly, an example of attaching the X-ray detector module 121 is explained. However, in the present embodiment, the worker can perform the operation more easily also when detaching the X-ray detector module 121.

That is to say, in the present embodiment, when the X-ray detector module 121 is detached, the guiding part 12121 of the support member 1212 is fitted to the guiding pin 1231 of the first fixing frame 123 similarly; thus, the X-ray detector module 121 is positioned in the radiation irradiation direction while the movement thereof in the channel direction and the row direction is restricted.

In the present embodiment, when the X-ray detector module 121 is detached from the fixing frame, the guidance groove 12125 of the support member 1212 is slidably supported by the jig attached to the guidance groove 12125 of the support member 1212 of the other attached X-ray detector module 121; thus, the X-ray detector module 121 is guided to move to the X-ray irradiation direction so as to be separated obliquely from the fixing frame.

As described above, in the present embodiment, the worker can exchange the radiation detector module more easily.

In the aforementioned embodiment, the guiding part 12121 is formed so that the cross section thereof orthogonal to the X-ray irradiation direction is a U-like shape; however, the embodiment is not limited to this shape. For example, the guiding part 12121 may have a trapezoidal or rectangular cross section that is orthogonal to the X-ray irradiation direction.

In the embodiment described above, the radiation detector and the radiation detector module according to the present disclosure are used for the X-ray CT apparatus; however, the embodiment is not limited thereto. For example, the radiation detector and the radiation detector module according to the present disclosure are similarly used for other medical image diagnosis apparatuses that utilize the radiation, such as a PET apparatus.

The term "processor" used in the above description refers to, for example, a central processing unit (CPU), a graphics processing unit (GPU), an application specific integrated circuit (ASIC), a simple programmable logic device (SPLD), a complex programmable logic device (CPLD), a field programmable gate array (FPGA), or the like. The processor achieves the function by reading out and executing a computer program in the memory 41. The computer program may be, instead of being saved in the memory 41, directly incorporated in the circuit of the processor. In this case, the processor achieves the function by reading and executing the computer program incorporated in the circuit. As for the processor in the present embodiment, a single circuit may be formed for each processor or one processor may be formed by combining a plurality of independent circuits to achieve the function. In addition, a plurality of elements in each drawing may be integrated into one processor to achieve the function.

In the embodiment and modifications described above, the function of each element of each device in the drawing is conceptual and the element is not necessarily structured physically as illustrated in the drawing. That is to say, the specific mode of the dispersion and integration of the devices is not limited to the illustrated ones and each device can be entirely or partially structured dispersed or integrated functionally or physically in an arbitrary unit in accordance with various kinds of loads or use situations, for example. Each processing function to be performed in each device may be entirely or arbitrarily partially achieved by the CPU or the computer program that is analyzed and executed in the CPU, or achieved as hardware by wired logic.

Among the processes described in the above embodiment and modifications, all or a part of the processes described to be performed automatically can be performed manually, or on the contrary, all or a part of the processes described to be performed manually can be performed automatically by a known method. In addition, the information including the process procedure, the control procedure, the specific names, various data and parameters, and the like, given in the document or illustrated in the drawings can be changed as appropriate unless specifically stated.

According to at least one embodiment described above, the worker can exchange the radiation detector module more easily.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A radiation detector comprising:
   a plurality of radiation detector modules, each radiation detector module including:
     a detection surface,
     a plurality of detecting elements configured to detect radiation and arranged on the detection surface in a channel direction and a row direction,
     a support member configured to support the plurality of detecting elements, and
     a guiding part with a groove shape formed at an end of the support member, the guiding part extending in a radiation irradiation direction;
   a fixing frame configured to fix positions of the plurality of radiation detector modules so that the plurality of radiation detector modules are arranged in the channel direction and attached and detection surfaces of the plurality of radiation detector modules are arranged in the channel direction;
   a guiding pin provided at an end of the fixing frame in the row direction, the guiding pin extending in the radiation irradiation direction; and
   wherein,
   when a radiation detector module of the plurality of radiation detector modules is attached to the fixing frame, the guiding part is fitted to the guiding pin so that the radiation detector module is positioned in the radiation irradiation direction while a movement thereof in the channel direction and the row direction is restricted.

2. The radiation detector according to claim 1, further comprising:
   a jig including a guidance part having an inclined surface; and
   the support member of each radiation detector module including a guidance groove formed at each side surface of the support member in the channel direction, the guidance groove having a sliding surface extending in the row direction; wherein,
   when the radiation detector module is attached to the fixing frame, the sliding surface in the guidance groove of the support member is slidably supported by the inclined surface that is provided, obliquely to the sliding surface, to the jig attached to a guidance groove of a support member of another attached radiation detector module, so that the radiation detector module is guided to move to the radiation irradiation direction so as to approach the fixing frame obliquely.

3. The radiation detector according to claim 2, wherein
   the jig is formed to have a stick-like shape and the guidance part that is formed to project in the channel direction from the support member when the jig is attached to the guidance groove of the support member along approximately an entire length in a longitudinal direction,
   the inclined surface of the guidance part that is formed to approach the fixing frame in the radiation irradiation direction from an end opposite to the guiding part to an end on a side of the guiding part in the row direction when the jig is attached to the guidance groove of the support member, and
   when the radiation detector module is attached to the fixing frame, the guidance groove of the support member moves in the row direction in a sliding contact with the inclined surface of the guidance part of the jig attached to the guidance groove of the support member of another attached radiation detector module, so that the radiation detector module is guided to move to the radiation irradiation direction so as to approach the fixing frame obliquely.

4. The radiation detector according to claim 1, further comprising:
a fixing member including a first screw; and
a second screw formed at an end of the guiding pin and configured to be engaged with the first screw, wherein,
with the guiding part fitted to the guiding pin, the radiation detector module is pressed to the fixing frame by the fixing member from a side opposite to the fixing frame by engaging the first screw of the fixing member with the second screw of the guiding pin, so that the radiation detector module is fastened to the fixing frame.

5. The radiation detector according to claim 1, wherein
the support member includes a positioning pin provided to a surface of the support member on a side that faces the fixing frame, the positioning pin projecting in the radiation irradiation direction,
the fixing frame includes a positioning hole provided to a surface of the fixing frame on a side that faces the support member, the positioning hole extending in the radiation irradiation direction, and
when the radiation detector module is attached to the fixing frame, the positioning pin of the support member is fitted to the positioning hole of the fixing frame with the guiding part fitted to the guiding pin, so that a position of the radiation detector module in the channel direction and the row direction is fixed.

6. A radiation detector module comprising:
a detection surface,
a plurality of detecting elements configured to detect radiation and arranged on the detection surface in a channel direction and a row direction,
a support member configured to support the plurality of detecting elements, and
a guiding part with a groove shape formed at an end of the support member, the guiding part extending in a radiation irradiation direction, wherein
the radiation detector module is attached to a fixing frame with other radiation detector modules, the fixing frame being configured to fix positions of a plurality of radiation detector modules so that detection surfaces of the plurality of radiation detector modules are arranged in the channel direction,
and
when the radiation detector module of the plurality of radiation detector modules is attached to the fixing frame, the guiding part is fitted to a guiding pin that is provided to an end of the fixing frame in the row direction and extends in the radiation irradiation direction, so that the radiation detector module is positioned in the radiation irradiation direction while a movement thereof in the channel direction and the row direction is restricted.

\* \* \* \* \*